United States Patent
Hassi

(10) Patent No.: US 10,527,496 B2
(45) Date of Patent: Jan. 7, 2020

(54) DETECTOR ASSEMBLY FOR ANALYSIS OF ELEMENTAL COMPOSITION OF A SAMPLE USING OPTICAL EMISSION SPECTROSCOPY

(71) Applicant: Hitachi High-Tech Analytical Science Limited, Abingdon, Oxfordshire (GB)

(72) Inventor: Jukka Hassi, Espoo (FI)

(73) Assignee: Hitachi High-Tech Analytical Science Limited, Abingdon (GB)

( * ) Notice: Subject to any disclaimer, the term of this patent is extended or adjusted under 35 U.S.C. 154(b) by 0 days.

(21) Appl. No.: 16/189,141

(22) Filed: Nov. 13, 2018

(65) Prior Publication Data

US 2019/0078935 A1   Mar. 14, 2019

Related U.S. Application Data

(63) Continuation of application No. 15/607,829, filed on May 30, 2017, now Pat. No. 10,197,445.

(30) Foreign Application Priority Data

May 30, 2016   (EP) .................................... 16171905

(51) Int. Cl.
| | | |
|---|---|---|
| *G01J 3/30* | (2006.01) | |
| *G01J 3/443* | (2006.01) | |
| *G01J 3/02* | (2006.01) | |
| *G01N 21/71* | (2006.01) | |
| *G01N 21/359* | (2014.01) | |
| *G01N 21/65* | (2006.01) | |

(52) U.S. Cl.
CPC ............. *G01J 3/443* (2013.01); *G01J 3/0208* (2013.01); *G01J 3/0237* (2013.01); *G01N 21/718* (2013.01); *G01J 3/0272* (2013.01); *G01N 21/359* (2013.01); *G01N 21/65* (2013.01); *G01N 2201/0221* (2013.01)

(58) Field of Classification Search
CPC ........ G01J 3/443; G01J 3/0208; G01J 3/0237; G01J 3/0272; G01N 21/718; G01N 21/359; G01N 21/65; G01N 2201/0221
USPC ......................................................... 356/318
See application file for complete search history.

(56) References Cited

U.S. PATENT DOCUMENTS

| | | | |
|---|---|---|---|
| 7,535,565 B1 | 5/2009 | Viertl et al. | 356/318 |
| 8,148,689 B1 | 4/2012 | Braunheim | 250/339.07 |
| 9,273,998 B2 * | 3/2016 | Myers | G01N 21/718 |

(Continued)

FOREIGN PATENT DOCUMENTS

| | | |
|---|---|---|
| EP | 1 063 512 A2 | 12/2000 |
| WO | WO 96/26431 | 8/1996 |

*Primary Examiner* — Tarifur R Chowdhury
*Assistant Examiner* — Jonathon Cook
(74) *Attorney, Agent, or Firm* — Harrington & Smith

(57) ABSTRACT

According to an example embodiment, a detector assembly for use in analysis of elemental composition of a sample by using optical emission spectroscopy is provided, the detector assembly comprising a rotatable element that is rotatable about an axis and that has attached thereto a laser source for generating laser pulses for invoking optical emission on a surface of the sample, which laser source is arranged to generate laser pulses focused at a predefined distance from said axis at a predefined distance from a front end of the detector assembly, and an optical receiver for capturing optical emission invoked by said laser pulses.

17 Claims, 6 Drawing Sheets

(56) References Cited

U.S. PATENT DOCUMENTS

| | | |
|---|---|---|
| 2012/0044488 A1 | 2/2012 | Senac .......................... 356/316 |
| 2012/0200415 A1* | 8/2012 | Braunheim ........ G01N 21/3563 340/600 |
| 2014/0204375 A1 | 7/2014 | Day .............................. 356/318 |
| 2015/0049339 A1 | 2/2015 | Tearney ....................... 356/479 |

* cited by examiner

DETECTOR ASSEMBLY FOR ANALYSIS OF ELEMENTAL COMPOSITION OF A SAMPLE USING OPTICAL EMISSION SPECTROSCOPY

CROSS-REFERENCE TO RELATED APPLICATION

This application is a continuation of U.S. patent application Ser. No. 15/607,829, filed May 30, 2017.

TECHNICAL FIELD

The present invention relates to an analyzer device for analysis of sample composition. In particular, embodiments of the present invention relate to portable analyzer devices for such a purpose.

BACKGROUND

Handheld or otherwise portable analyzer devices are frequently used in the field e.g. for recognizing and sorting objects according to material(s) they contain. As a few examples, a portable analyzer device may be used in places like scrapyards, dumping grounds and recycling centers, while they also have more generic commercial and industrial use.

While several techniques for analyzing a sample under study are available for in analyzer devices of such type, optical emission spectroscopy is widely employed in portable analyzer devices to determine elemental composition of the sample under study. Herein, such analyzer devices are referred to as optical analyzers. An optical analyzer typically includes an excitation assembly for invoking an optical emission from a surface of a sample under study, a detector assembly for capturing signals that are descriptive of the optical emission so invoked, and an analysis means for determining elemental composition of the sample under study on the basis of the captured signals.

Laser-induced breakdown spectroscopy (LIBS) is widely used technique for optical emission spectroscopy, and an analyzer device making use of LIBS may be referred to as a LIBS analyzer. In a LIBS analyzer, the excitation means comprises a laser source that is arranged to generate a high peak power laser pulse. The laser pulse is focused to the sample under study to form a plasma plume on a surface of the sample in order to cause atomization and excitation on the surface. This causes light emission at wavelength(s) that are characteristic to elements on the surface of the sample. The signal descriptive of the light emission from the sample are captured at the detector means, which then passes the captured signals for the analysis means for determination of the elemental composition of the sample. Since all elements emit light that exhibit wavelength(s) characteristic thereto in response to such excitation, the relative intensities of different wavelengths indicated in the captured signals reveal the elemental constitution of the sample.

Another example of optical emission spectroscopy is Raman spectroscopy that includes a laser source as the excitation means to invoke electromagnetic radiation from the sample, which electromagnetic radiation is captured by the detector means. A further example of optical emission spectroscopy is near infrared (NIR) spectroscopy, which is a special case of Raman spectroscopy where the excitation means includes a NIR laser.

In the framework of optical emission spectroscopy that relies on a laser as the excitation means, the laser beam needs to be focused on the surface of the sample in order to effectively invoke the optical emission from the sample. Moreover, in order to ensure reliable analysis due to small variations in composition of the sample on its surface, during an analysis cycle the laser beam is moved to cover an area of the sample surface instead of focusing the laser beam in a single spot on the surface of the sample. This ensures that possible small variations in composition of the sample are 'averaged' over the area, thereby resulting in a more reliable analysis result.

In known solutions, the laser beam is moved along the surface of the sample during an analysis cycle by moving an optical component (e.g. a mirror or a focusing lens) via which the laser beam is guided on the surface of sample or by tilting a laser assembly about a pivot axis. However, moving the optical component or tilting the laser assembly about the pivot axis creates an arc-like movement of the laser beam with respect to the sample surface and hence results in changing the distance between the laser source and the surface of the sample. Consequently, the laser beam is not correctly focused on the surface of the sample over the whole analysis cycle. This typically leads into inefficient production of optical emission from the surface of the sample (e.g. in case of LIBS out-of-focus laser beam results in inefficient plasma formation on the surface of the sample), which in turn is likely to result in reduced accuracy and/or reliability of the analysis.

SUMMARY

It is therefore an object of the present invention to provide an arrangement for laser-induced optical emission spectroscopy that enables maintaining or substantially maintaining correct focus of the laser beam throughout the analysis cycle.

In the following, a simplified summary of some embodiments of the present invention is provided in order to facilitate a basic understanding of various embodiments of the present invention. The summary is, however, not an extensive overview of the invention. It is neither intended to identify key or critical elements of the invention nor to delineate the scope of the invention. The following summary merely presents some concepts of the invention in a simplified form as a prelude to a more detailed description of exemplifying embodiments of the invention.

According to an example embodiment, a detector assembly for use in analysis of elemental composition of a sample by using optical emission spectroscopy is provided, the detector assembly comprising a rotatable element that is rotatable about an axis and that has attached thereto a laser source for generating laser pulses for invoking optical emission on a surface of the sample, the laser source arranged to generate laser pulses focused at a predefined distance from said axis at a predefined distance from a front end of the detector assembly, and a detector element for capturing optical emission invoked by said laser pulses.

According to another example embodiment, an analyzer device for analysis of elemental composition of a sample is provided, the device comprising a detector assembly according to the example embodiment outlined in the foregoing for invoking an optical emission from a surface of the sample, wherein the detector element is arranged to record one or more detection signals that are descriptive of at least one characteristic of said optical emission for analysis of elemental composition of the sample by an analysis means, and control means for initiating an analysis cycle in response to a trigger signal, the control means arranged to cause the following during the analysis cycle: rotate the rotatable element, operate the laser source to generate one or more laser pulses during rotation of the rotatable element, and operate the detector element to record one or more detection signals during rotation of the rotatable element.

According to another example embodiment, a method for operating a detector assembly according to the example embodiment outlined in the foregoing is provided, wherein the detector element is arranged to record one or more detection signals that are descriptive of at least one characteristic of said optical emission for analysis of elemental composition of the sample by an analysis means, the method comprising rotating the rotatable element, operating the laser source to generate one or more laser pulses during rotation of the rotatable element, and operating the detector element to record one or more detection signals during rotation of the rotatable element.

The novel features which are considered as characteristic of the invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF DRAWINGS

In the accompanying drawings.

DETAILED DESCRIPTION

Figure 1:
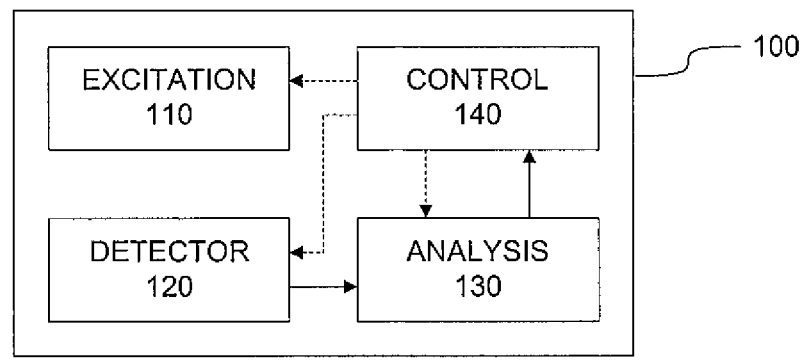
FIG. 1 illustrates a block diagram of some components of an analyser for analysis of elemental composition of a sample according to an example embodiment.

FIG. 1 illustrates a block diagram of some (logical) components of an analyser 100 for analysis of elemental composition of a sample according to an example. Therein, the analyser 100 comprises an excitation means 110 for invoking an optical emission from a surface of a sample under study, a detector means 120 for recording at least one detection signal that is descriptive of one or more characteristics of the optical emission invoked from the surface of the sample, analysis means 130 for determining elemental composition of the sample on basis of one or more recorded detection signals, and control means 140 for operating the excitation means 110, the detector means 120 and the analysis means 130 to carry out a spectral analysis to determination of the elemental composition of the sample. The control means 140 is communicatively coupled (e.g. by one or more electrical wires or electrical connectors of other type) to the excitation means 110, to the detector means 120 and to the analysis means 130 to enable controlling operation of these components. In the example of FIG. 1, the dashed lines denote control signals and solid lines denote flow of (other) information. In other examples, the analysis means 130 may be, at least in part, integrated to the detector means 120 and/or to the control means 140.

Figure 2A:
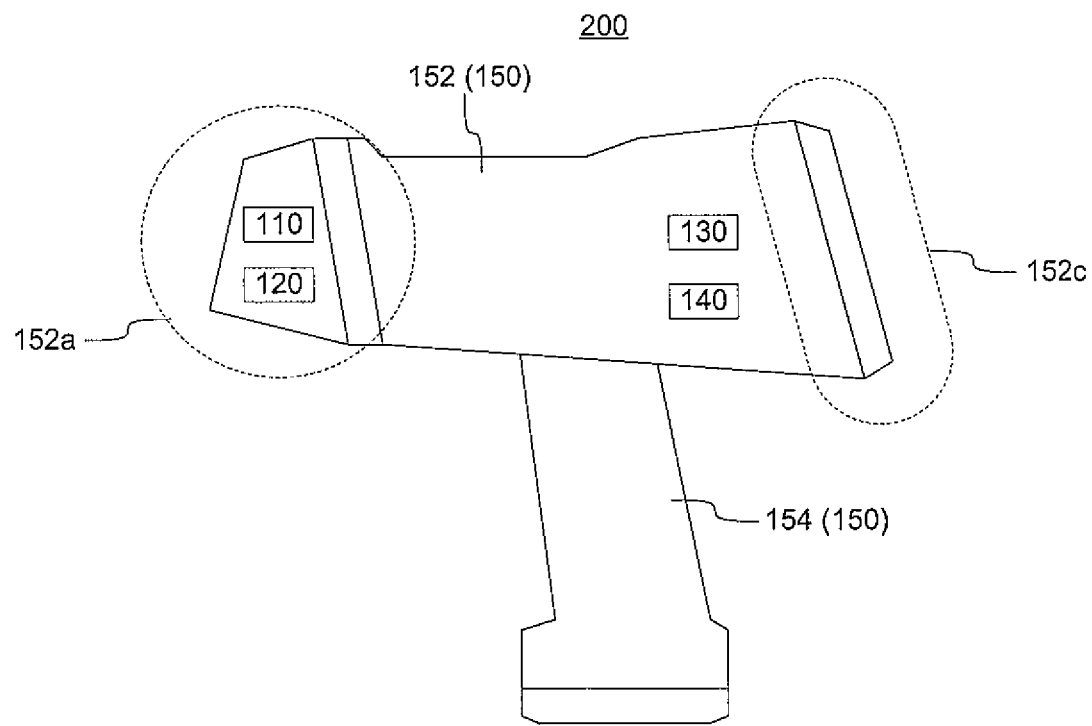
FIG. 2A schematically illustrates arranging some components of an analyser for analysis of elemental, composition of a sample into a casing of a portable analyzer device according to an example.

There is a plurality of ways to provide the analyzer 100 is part of an analyzer device. In this regard, FIG. 2A illustrates a non-limiting example of arranging the components of the analyzer 100 in a casing 150 of a portable analyzer device 200. The illustration of FIG. 2A schematically depicts a side view to the casing 150, which, at least conceptually, includes two parts: a body 152 for housing at least the excitation means 110 and a handle 154 for holding the portable analyzer device 200 when it is in use. When using the portable analyzer device 200, the user typically grabs the handle 154 with one hand and points a front part 152a of the body 152 away from himself/herself, against or close to the sample under analysis. Therefore, in the portable analyzer device 200, both the excitation means 110 and the detector means 120 are arranged in the front part 152a to enable effective excitation of the object under analysis by the excitation means 110 and effective capturing of the optical emission invoked on the surface of the sample under analysis by the detector means 120, whereas the analysis means 130 and the control means 140 provided elsewhere in the body 152.

Figure 2B:
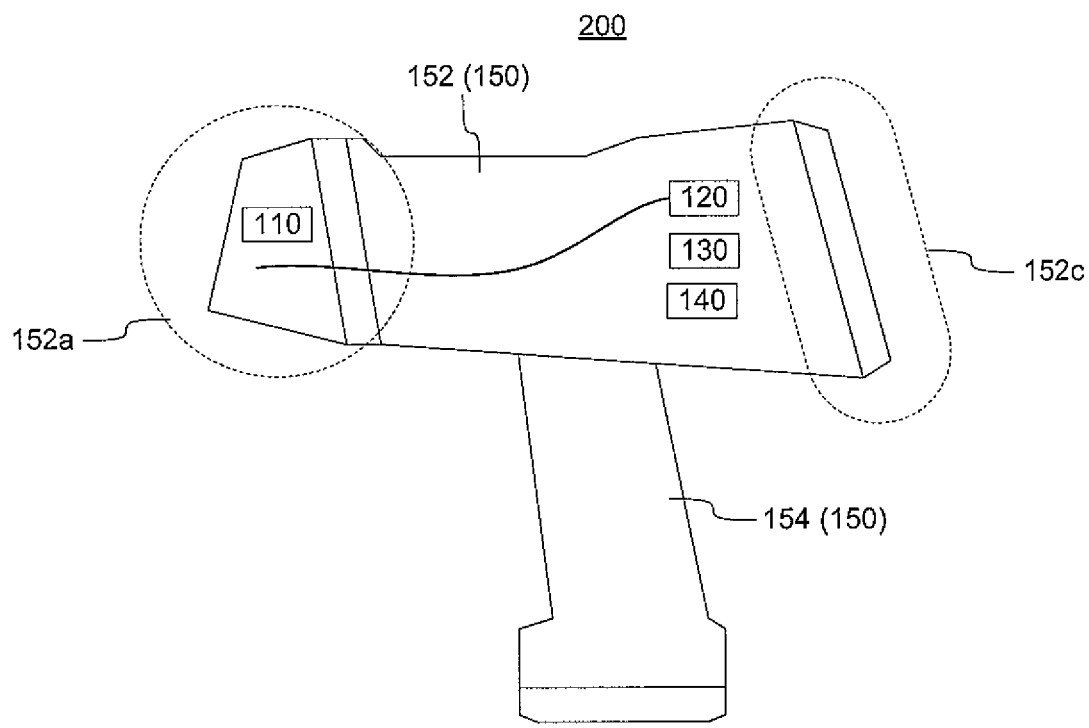
FIG. 2B schematically illustrates arranging some components of an analyser for analysis of elemental composition of a sample into a casing of a portable analyzer device according to an example.

In another example, schematically illustrated in FIG. 2B, the arrangement of the detector means 120 may be varied from that shown in the example of FIG. 2A such that the front part 152a houses an optical receiver for receiving the optical emission invoked on the surface of the sample, whereas the detector means 120 is arranged in some other location within the casing 150, e.g. in or close to a rear part 152c of the body 152 or in the handle 154. The optical receiver is optically coupled to the detector means 120 by an optical fiber cable or by other suitable means for optical coupling. The optical receiver may simply comprise an end of the optical fiber cable (or an end of another means of optical coupling), which may be further covered by a lens or a transparent cover (made of glass or plastic) for protection against dust, dirt and other impurities in the operating environment of the portable analyzer device 200. The optical receiver may also employ focusing optical elements such as mirrors or lenses to more efficiently collect and couple light into the detector means 120.

The portable analyzer device 200 may further comprise a number of components that are typical for corresponding analyzers known in the art, including user input means for receiving input from a user and user output means for providing output to the user. The user input means may comprise, for example, one or more keys, buttons or knobs, a touchscreen, a touchpad, etc. to enable receiving user input to configure operating parameters of the portable analyzer device 200 according to analysis task at hand. The output means may comprise a display means for displaying information to the user, such as e.g. an electronic visual display, a touchscreen, one or more light indicators (e.g. LEDs) etc. The display means may be employed, for example, to provide information concerning the result of the analysis, operational state of the portable analyzer device 200 and/or indication(s) regarding current settings of operating parameters of the portable analyzer device 200. The output means may comprise, additionally or alternatively, a sound reproduction means for providing audible information to the use. The audible information may include, for example, sounds or signals that are descriptive of operational state of the portable analyzer, indication(s) regarding current settings of operating parameters of the portable analyzer device 200 and/or initialization/completion of the analysis triggered by the user.

The portable analyzer device 200 is typically also provided with a dedicated trigger means that enable the user to initiate analysis of the sample. Conceptually, the trigger means may be part of the user input means, although due to its special function it may be provided separately from main part of the user input means. In particular, the trigger means may be arranged in a front side of the handle 154 to make it readily accessible by the user e.g. by pressing it using the index finger of the hand holding the handle 154. The user input means and the user output means, to extent they are present in the analyzer device 200, are preferably arranged in the casing 150 such that they are conveniently accessible by the user when the portable analyzer device 100 is in use, e.g. in an upper part of the body 152 and/or in the rear part 152c.

The excitation means 110 comprises a laser source that is arranged to generate one or more laser pulses under control of a trigger signal issued by the control means 140. In an example, the analyzer 100 relies on a laser-induced breakdown spectroscopy (LIBS) known in the art, thereby rendering the analyzer 100 as a LIBS analyzer. In a LIBS analyzer, the laser source is arranged to generate a series of one or more laser pulses under control of the trigger signal. In other examples, a laser excitation based technique of optical emission spectroscopy different from LIBS may be employed, such as Raman spectroscopy or NIR spectroscopy known in the art. In such scenarios the characteristics and/or operation of the laser source in the excitation means 110 may be different. Throughout the following description, explicit and/or implicit references to the LIBS technique may be included. LIBS, however, serves as a non-limiting example of a framework within which various examples embodiments of the present invention may be provided.

The trigger signal that initiates generation of the laser pulse(s) in the excitation means 110 may specify characteristics of the laser pulse(s), e.g. the number of pulses to generated, repetition rate/frequency of the pulses to be generated (if more than one pulses are to be generated) and/or power/energy of the pulse(s) and the excitation means 110 may control generation of laser pulse(s) from the laser source accordingly. Moreover, the trigger signal may further specify characteristics such as duration of the pulse(s), wavelength(s) to be applied in the pulse(s), bandwidth of the pulse(s) and the excitation means 110 may include mechanism(s) for adjusting the pulses accordingly. Instead of receiving indication(s) of characteristics of the laser pulse(s) to be generated in the trigger signal, at least some of these characteristics may be predefined such that the excitation means serves to generate laser pulse(s) of predefined number and/or characteristics upon reception of the trigger signal. In this latter scenario, the trigger signal may simply serve as an indication to generate the laser pulse(s) according to the predefined characteristics.

At least some elements of the excitation means 110 and the detector means 120 may be provided in a detector assembly or a detector unit that includes one or more elements or components that serve to provide the excitation means 110 and one or more elements or components that serve to provide the detector means 120. Along the lines described in the foregoing in context of the portable analyzer device 200, the detector assembly may be arranged in the front part 152a of the body 152 of the casing 150 of the portable analyzer device 200, thereby providing the excitation means 110 and the detector means 120 in the front part.

Figure 3C:
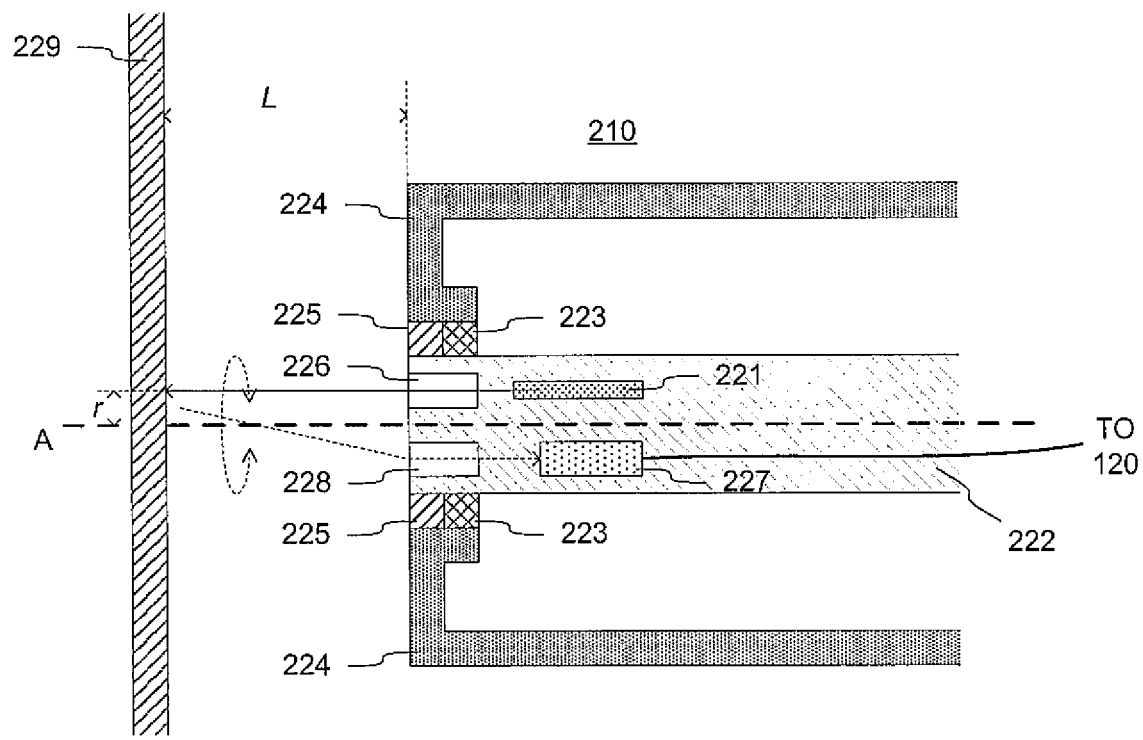
FIG. 3C schematically illustrates some components of a detector assembly according to an example embodiment.
Figure 3A:
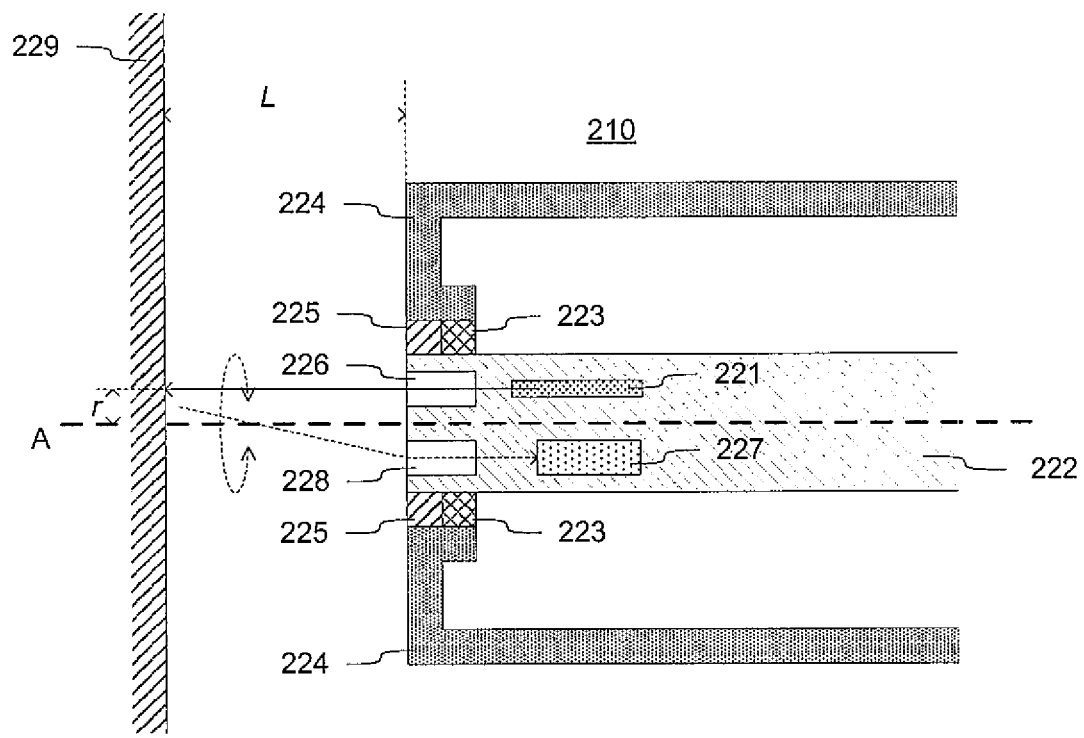
FIG. 3A schematically illustrates some components of a detector assembly according to an example embodiment.
Figure 3B:
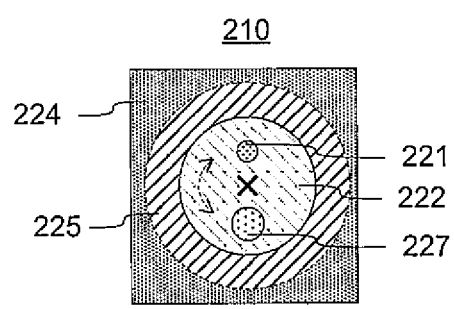
FIG. 3B schematically illustrates some components of a detector assembly according to an example embodiment.

FIGS. 3A and 3B schematically illustrate some components of a detector assembly 210 according to an example: FIG. 3A depicts a cross-section of the detector assembly 210 together with a sample 229 and FIG. 3B depicts a front view of the detector assembly 210. The detector assembly 210 comprises a rotatable element 222 that is rotatable about an axis A, which axis is indicated by a dashed line in FIG. 3A and by a cross in FIG. 3B). The rotatable element 222 is attached to a housing 224 of the detector assembly 210 via a bearing 223. In general, the bearing 223 has an opening into which the rotatable element 222 or part thereof is mounted to enable rotating movement with respect to the housing 224. In an example described with respect to various details in the following, the bearing 223 is provided as a rolling bearing that has its outer race attached to the housing 224 and its inner race attached to the rotatable element 222, thereby enabling smooth rotating movement of the rotatable element 222 with respect to the housing 224. However, in other examples the bearing may be provided as a bearing of other type that enables rotating movement of the rotatable element 222, e.g. as a plain bearing.

A laser source 221 for generating laser pulses is arranged in the rotatable element 222 such that the laser beam hits a surface of the sample 229 off-axis, at a distance r (where r>0) from the axis A. The rotatable element 222 may also be referred to as a rotatable body or a rotatable component. The direction of the laser beam is indicated in FIG. 3A by an arrow extending from the laser source 221, and the end (or side) of the detector assembly 210 from which the laser beam exits therefrom and which is intended to face the sample 229 when operating the detector assembly 210 e.g. in the analysis device 200 for analysis of the sample 229, may be referred to as a front end of the detector assembly 210. Along similar lines, the end of the rotatable element 222 from which the laser beam exits therefrom may be referred to as a front end of the rotatable element 222.

In the example of FIG. 3A, the laser beam is transmitted from the laser source 221 to the sample surface via a beam focusing arrangement 226 that is arranged to focus and/or guide the laser beam to the desired distance r from the axis A on a(n imaginary) plane that is perpendicular to the axis A at a predefined distance L from the front end of the detector assembly 210, where the distance L represents the intended (e.g. assumed) distance between the front end of the detector assembly 210 and the surface of the sample 229 when operating the detector assembly 210 for analysis. The beam focusing arrangement 226 preferably comprises an optical focusing arrangement that may comprise one or more lenses, one or more mirrors, or a combination of one or more lenses and one or more mirrors. Such optical focusing arrangements are well-known in the art and therefore details thereof are hence not discussed in more detail herein.

FIGS. 3A and 3B further show an optical detector element 227 for capturing the optical emission invoked on the surface of the sample 229 to enable recording at least one detection signal that is descriptive of one or more characteristics of the optical emission for provision for analysis in the analysis means 130 (e.g. by a spectrometer). In the example shown in FIG. 3A, the optical detector element 227 may comprise the detector means 120 that is (electrically) coupled to the analysis means 130 provided outside the rotatable element 222. As another example, as described in the foregoing, the rotatable element 222 may be provided with an optical receiver for receiving the optical emission invoked on the surface of the sample, which optical receiver is optically coupled to the detector means 120 by an optical fiber cable or by other suitable means for optical coupling. Hence, as schematically illustrated in FIG. 3C, in this example the optical detector element 227 may comprise the optical receiver that is coupled to the detector means 120 provided outside the rotatable element 222 and further to the analysis means 130 via an optical fiber cable.

The rotatable element 222 is further provided with a detector focusing arrangement 228 that is arranged to focus and/or guide the optical emission from the surface of the sample 229 to the detector element 227 for efficient capture of the optical emission. The detector focusing arrangement 228 is arranged to focus and/or guide the optical emission in view of the distance L from the front end of the detector assembly 210 and further in view of the position of the detector element 227 with respect to the axis A and the distance r from the axis A. The detector focusing arrangement 228 preferably comprises an optical focusing arrangement that may comprise one or more lenses, one or more mirrors, or a combination of one or more lenses and one or more mirrors (as known in the art).

Arranging elements of the detector means 120 (e.g. the detector element 227 and the detector focusing arrangement 228) in the rotatable element 222 together with elements of the excitation means 110 (e.g. the laser source 221 and the beam focusing arrangement 226) is beneficial in that it ensures fixed position of elements of the detector means 120 with respect to the point where the laser beam from the laser source 221 hits the surface of the sample 229 regardless of rotational position of the rotatable element 222, which facilitates reliable and uniform detection performance while rotating the rotatable element 222.

Although the beam focusing arrangement 226 and the detector focusing arrangement 228 are depicted in FIG. 3A as separate elements, in an example the beam focusing arrangement 226 and the detector focusing arrangement 228 share one or more components. As a particular example, in an optical focusing arrangement that serves to provide both the beam focusing arrangement 226 and the detector focusing arrangement 228, one or more lenses and/or mirrors may be shared between the beam focusing arrangement 226 and the detector focusing arrangement 228. Such optical focusing arrangements are known in the art.

The front end of the rotatable element 222 may be covered at least in part by a radiation window (not explicitly shown in FIGS. 3A and 3B) through which the laser beam from the laser source 221 exits the detector assembly 210 and through which the optical emission enters the detector assembly 210. The radiation window transmits most of the radiation energy generated by the laser source 221 and transmits the generated optical emission at least at wavelengths of interest. The radiation window also serves to prevent dust, dirt and other impurities as well as moisture possibly present in the operating environment of the detector assembly 210 from entering the housing 224. Radiation windows suitable to serve this purpose are known in the art.

FIG. 3A depicts a non-limiting example where the laser source 221 is arranged at the distance r from the axis A to emit the laser beam in a direction that is parallel with the axis A. This is, however, a non-limiting example of providing the laser beam such that it hits the surface of the sample 229 at the distance r from the axis A. Some further examples in this regard are described in the following with references to FIGS. 4 to 6.

Figure 4:
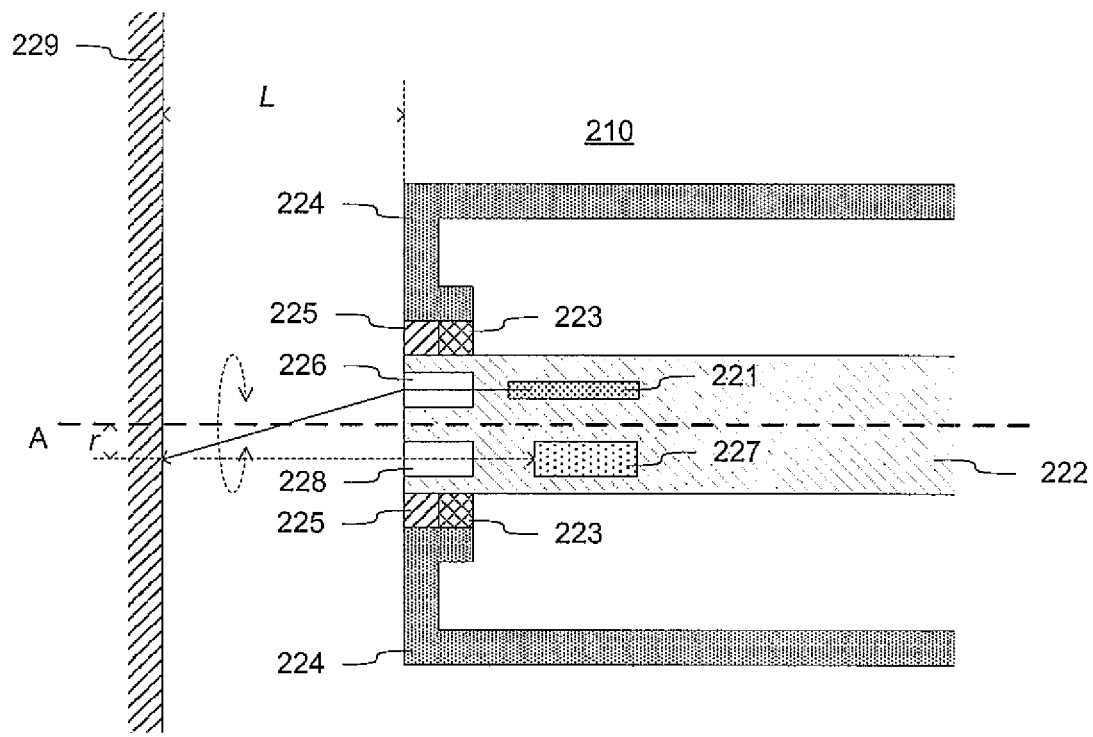
FIG. 4 schematically illustrates some components of a detector assembly according to an example embodiment.
Figure 5:
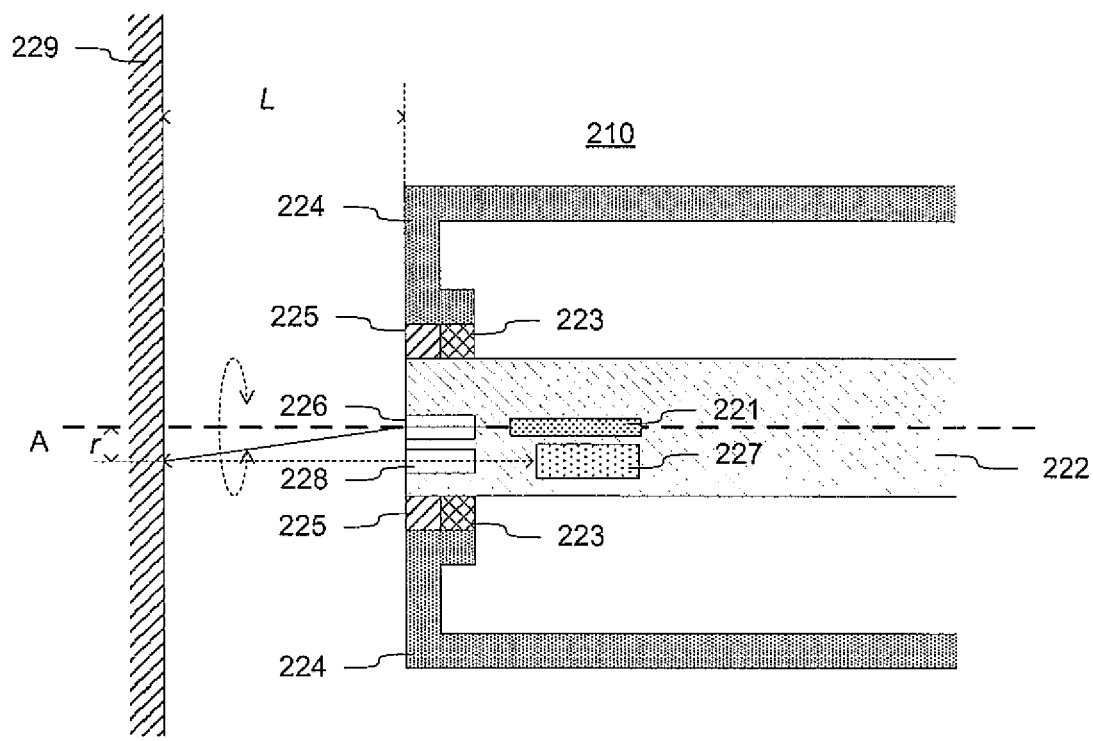
FIG. 5 schematically illustrates some components of a detector assembly according to an example embodiment.
Figure 6:
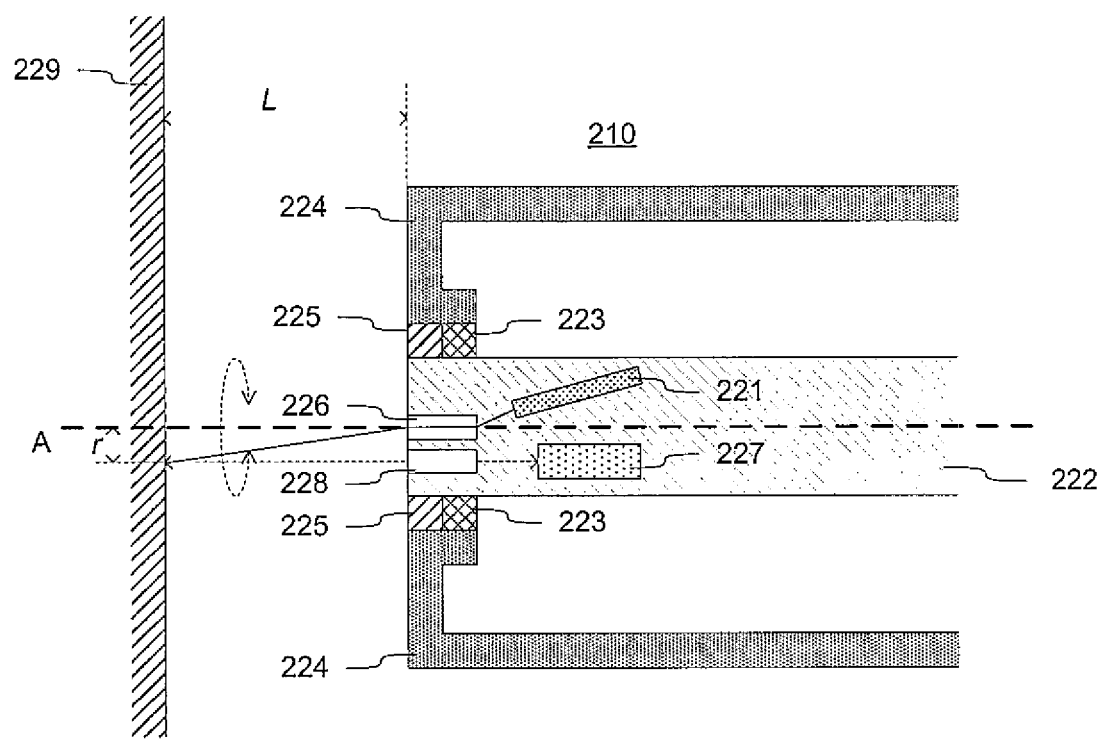
FIG. 6 schematically illustrates some components of a detector assembly according to an example embodiment.

In the example of FIG. 4, the laser source 221 arranged off the axis A (by a distance that may be different from the distance r) generates a laser beam that is parallel or substantially parallel with the axis A, while the beam focusing arrangement 226 is arranged to focus, reflect and/or refract the laser beam to hit the surface of the sample 229 at the distance r from the axis A at the distance L from the front end of the detector assembly 210. In the example of FIG. 5, the laser source 221 arranged in the axis A generates a laser beam that is aligned or substantially aligned with the axis A, while the beam focusing arrangement 226 is arranged to focus, reflect and/or refract the laser beam to hit the surface of the sample 229 at the distance r from the axis A at the distance L from the front end of the detector assembly 210. In the example of FIG. 6, the laser source 221 arranged off the axis A (by a distance that may be different from the distance r) generates a laser beam that is not in parallel or substantially parallel with the axis A (e.g. there is a non-zero angle between the axis A and the trajectory of the laser beam between the laser source 221 and the beam focusing arrangement 226), while the beam focusing arrangement 226 is arranged to focus, reflect and/or refract the laser beam to hit the surface of the sample 229 at the distance r from the axis A at the distance L from the front end of the detector assembly 210.

In the examples of FIGS. 3A to 6 the front end of the rotatable element 222 is aligned or substantially aligned with the front end of the detector assembly 210 (e.g. the front surface of the housing 224). When providing such detector assembly 210 as part of the analyser device 200, the detector assembly 210 is arranged in the front part 152a such that the front end of the detector assembly 210 is set to the distance L from the surface of the sample 229 when the front part 152a is held against the sample 229. As an example in this regard, the front part 152a in the body 152 of the casing 150 may be provided with a recess that has depth that is equal or substantially equal to the distance L, and the detector assembly 210 is arranged within the casing 150 such that its front end is aligned or substantially aligned with the part of the casing 150 that forms the 'bottom' of the recess, thereby setting the front end of the rotatable element 222 at the distance L from the front end of the front part 152a (and hence sets the front end of the detector assembly 210 at the distance L from the sample 229 when the analyser device 200 is held against the sample 229).

In other examples, the rotatable element 222 may be recessed with respect to the front end of the detector assembly 210 (e.g. the front surface of the housing 224) by a distance K. Conceptually, the examples of FIGS. 3A to 6 may be considered to have K=0. Recessing the rotatable element 222 such that its front end is arranged at non-zero distance K from the front end of the detector assembly 210 enables making the distance L smaller, thereby enabling analyser device 220 structure where the depth of the recess in which the detector assembly 210 is installed is smaller. In one example, the distance L may be zero, thereby causing the laser beam to be focused on a plane that is aligned with the front end of the detector assembly 210. In such an arrangement, part of the housing 224 that constitutes the front end of the detector assembly 210 may form at least part of the front end of the front part 152a of the casing 150.

In the illustrations of FIGS. 3A to 6, the rotatable element 222 is depicted as a cylindrical or substantially cylindrical element having the axis A as its axis, where the laser source 221, the beam focusing arrangement 226, the detector element 227 and the detector focusing arrangement 228 are arranged inside the cylindrical element. The diameter of such cylindrical element is selected such that it matches the size of the opening in the bearing 223 (e.g. the size of the inner race of the bearing) and hence provides a mechanically strong and durable attachment between the cylindrical element and the bearing 223, which is beneficial when making use of the detector assembly 210 e.g. in the portable analyzer device 200 (or in a corresponding analyzer device) intended for field use.

However, the cylindrical or substantially cylindrical shape of the rotatable element 222 applied in the illustrations of FIGS. 3A to 6 serve as a non-limiting conceptual example, selected for graphical clarity of illustrations. The rotatable element 222 may have any desired shape and size that can be securely mounted to the opening in the bearing 223 (e.g. to the inner race of a rolling bearing), as long as the rotatable element 222 is able to rotate within the housing 224 to a desired extent. In this regard, the rotatable element 222 may be considered to include a fitting portion that matches the size and shape of the opening in the bearing 223 to enable secure and mechanically durable attachment thereto and a body portion extending from the fitting portion away from the front end of the detector assembly 210. As a few (non-limiting) examples, the fitting portion may comprise a cylindrical element whereas the body portion may comprise a rod, a plate or another structural element extending from the fitting portion.

In addition to providing a secure mounting to the bearing 223, the fitting portion serves to carry a mechanical load constituted by the body portion and components of the detector assembly 210 attached to the fitting portion or to the body portion. Furthermore, the radiation window typically attaches to the fitting portion of the rotatable element 222. The optical components, e.g. laser source 221, the detector element 227, the beam focusing arrangement 226 and/or the detector focusing arrangement 228, are typically attached to the body part.

When pointing the detector assembly 210 towards a sample under analysis such that the axis A is perpendicular or substantially perpendicular to the sample surface, the rotating movement of the rotatable element 222 moves the point at which a laser beam from the laser source 221 hits the surface of the sample 229 in a lateral direction, i.e. along a circular trajectory having the radius r on the surface of the sample 229. Consequently, the distance between the point from which the laser beam exits the detector assembly 210 (e.g. the beam focusing arrangement 226) and the surface of the sample 229 remains constant, i.e. at the distance L, regardless of the 'phase' of rotation of the rotatable element 222.

FIGS. 3A and 4 to 6 further show a seal 225 that serves to isolate the space within the housing 224 from its environment in a dust-proof and splash-proof manner, thereby contributing towards preventing dust, dirt and other impurities as well as moisture possibly present in the operating environment of the detector assembly 210 from entering the housing 224 and hence from degrading operation of optical and electrical components arranged in inside the housing 224. The seal 225 may be a component that is separate from the bearing 223, or the seal 225 may be a built-in component of the bearing 223. Instead of sealing the space within the housing 224 only from the outside (i.e. on the side of the front end of the detector assembly 210), the seal 225 may comprise a respective seal component on both sides of the bearing 223.

The housing 224 has an opening for mounting the bearing 223 and the front end of the rotatable element 222 therein. The opening hence also enables laser pulses generated by the laser source 221 to exit and the optical emission invoked at the surface of the sample 229 to enter the detector assembly 210. In case the front end of the rotatable element is not provided with the radiation window (as described in the foregoing), the opening in the housing 224 may be at least in part covered by a radiation window, through which the laser beam from the laser source 221 exits the detector assembly 210 and through which the optical emission enters the detector assembly 210.

In an example, the opening in the housing 224 is a circular or substantially circular opening having a size matching or substantially matching size (e.g. diameter) of the front end of the rotatable element 222. Although using herein an opening of circular or substantially circular shape as an example, in general the opening in the housing 224 may have any suitable shape that enables laser pulses from the laser source 221 to exit and the optical emission to enter the detector assembly 210 therethrough regardless of rotational position of the rotatable element 222.

The detector assembly 210 comprises or is otherwise provided with actuator means that enable inducing rotating movement to the rotatable element 222 under control of the trigger signal (received from or via the control means 140). Several mechanisms for serving as the actuator means are known in the art. The actuator means may comprise, for example, a stepper motor, a servo feedback motor or a piezo motor, connected to the rotatable element 222 via a suitable transmission arrangement for conveying the movement generated by the motor into a rotating movement of the rotatable element 222. In an example, the transmission arrangement comprises a gear and a pinion, arranged to convey the movement generated by the motor to the rotatable element 222 via a segment of spur gear arranged on the rotatable element 222 (e.g. on an outer surface of the fitting portion). In other examples, the transmission arrangement may comprise a belt drive arrangement or a worm drive arrangement, configured to convey the rotating movement to the rotatable element 222 via the fitting portion thereof. The direction, speed and extent of rotating movement induced to the rotatable element 222 may be predefined, or the direction, speed and/or extent of the rotating movement may be indicated in the trigger signal. The rotating movement can be induced at a relative low energy with a good accuracy with respect to direction, speed and extent of rotation, thereby enabling good control over the trajectory of the position of the laser beam on the surface of the sample 229.

The distance r between the axis A (i.e. the axis of rotation of the rotatable element 222) and the focus point of the laser beam from the laser source 221 (on the surface of the sample 229) is set on basis of the desired extent of the circular trajectory of the point where the laser beam from the laser source 221 hits the surface of the sample 229, possibly in view of the speed and/or extent of rotating movement applied during an analysis cycle (which is a concept described in more detail in the following).

In an example, the rotatable element 222 may enable free rotating movement about its axis. However, enabling rotation to such an extent typically requires a complex electrical and/or optical coupling between components attached to the rotatable element 222 and other components of the detector assembly 210 and/or other components of an analyser device, e.g. the portable analyser device 200, making use of the detector assembly 210. Therefore, in another example, the rotation of the rotatable element 222 is limited to allow for a more straightforward electrical and/or optical coupling between components attached to the rotatable element 222 and other components of the detector assembly 210 and/or other components of an analyser device (e.g. by electrical wire(s) and/or optical fibre cable(s) of sufficient length that allow for rotation to the desired extent). As a few examples, the rotation of the rotatable element 222 is limited e.g. to one full cycle of rotation, to half of a full cycle of rotation or to another predefined fraction of a full cycle of rotation. As an example in this regard, the predefined fraction of the full cycle may be for example a value selected from a range from 5 to 45 degrees, e.g. 10 degrees or 20 degrees, wherein the selection may be made at least in part on dependence of the distance r and/or the distance L.

When operating the detector assembly 210 is part of the analyser 100, e.g. in context of the portable analyser device 200 (or a corresponding analyser device), the trigger signal initiates an analysis cycle that involves one set of measurements that enables the detector means 120 to record the detection signals that enable analysis of the elemental composition of the sample by the analysis means 130. During the course of an analysis cycle, the rotatable element 222 in the detector assembly 210 is rotated according to desired rotation characteristics while the laser source 221 therein is operated to generate laser pulse(s) of desired pulse characteristics and the detector element 227 is operated to record one or more detection signals during the course of rotating movement of the rotatable element 222. In this regard, as described in the foregoing, the desired laser characteristics such as the number and/or characteristics of the generated laser pulse(s) may be predefined or the detector assembly 210 may receive indication of the number and/or characteristics of the laser pulses to be generated in the trigger signal. Along similar lines, as also described in the foregoing, the desired rotation characteristics such as the direction of rotation, the extent of rotation and/or the rotation speed during the analysis cycle may be predefined or the direction of rotation, the extent of rotation and/or the rotation speed during the analysis cycle may be specified in the trigger signal.

In the following, some aspects related to generation of laser pulses and capturing detection signals (e.g. measurement values) while the rotatable element 222 is being rotated according to the desired rotation characteristics are described in an exemplifying and non-limiting manner. Herein, the detector assembly 210 may be employed to carry out an analysis cycle in context of LIBS analysis. While the rotatable element 222 is rotated according to the desired rotation characteristics, the laser source 221 is operated to produce short laser pulses (having duration in a range of a few nanoseconds) with pulse energy of a pulse set in a desired value in the range of 5 µJ-50 mJ. A desired repetition rate of laser pulses (i.e. the pulse frequency) may be chosen from the range of 10-10000 Hz. The rotation speed of the rotatable element 222 may be selected, at least partially in view of the repetition rate of the laser pulses, to obtain a desired level of overlap between the successive laser pulses. The desired level of overlap can range from a substantial overlap (e.g. in order to first clean the surface of the sample 229) to essentially zero (in order to measure only fresh spots on the surface of the sample 229). While the rotatable element 222 is rotated according to the desired rotation characteristics, the detector element 227 is operated to capture a set of detection signals (e.g. measurement values) for the analysis cycle. The analysis cycle may be divided in to a sequence of sub-periods of predefined temporal length (i.e. duration), and each detection signal may be captured during a respective sub-period of the analysis cycle. Duration of the sub-period may be a desired value selected e.g. from the range of 2 to 30 milliseconds (ms). A detection signal derived for a given sub-period may be descriptive of at least one characteristic of optical emission captured by the detector element 227 during the given sub-period, obtained e.g. by averaging or integrating the at least one characteristic of optical emission detected during the given sub-period by deriving the at least one characteristic on basis of optical emission that is averaged or integrated over the given sub-period.

Typical measurement times, i.e. analysis cycle durations, for LIBS analysis by using a portable (e.g. handheld) analyser device range from 0.5-30 seconds, and during this time rotation operation of desired characteristics can be arranged to take place a desired number of times, e.g. once or multiple times. As the laser beam passes over an already measured part of the surface of the sample 229 it may be advantageous to either (1) average the results from the multiple passes, or (2) separately analyse the results from each pass in order to avoid a potential surface contribution to the analysis results. In implementation non-limiting example, the repetition rate of the laser pulses is 5 kHz, the movement range of the laser beam on the surface of the sample 229 is approximately 3 mm, and the total measurement time (i.e. the analysis cycle duration) is 600 ms in one direction of rotation.

Due to the arrangement of the focus point of the laser beam from the laser source 221 off-axis at the distance r from the axis of rotation of the rotatable element 222, the laser beam excites the sample surface on multiple points while the distance between the front end of the detector assembly 210 and the surface of the sample 229 remains constant throughout the analysis cycle. Consequently, all detection signals recorded by the detector means 120 during the analysis cycle can be obtained with correct focus distance between the detector assembly 210 and the surface of the sample 229, which contributes towards more accurate and reliable detection results.

Figure 7:
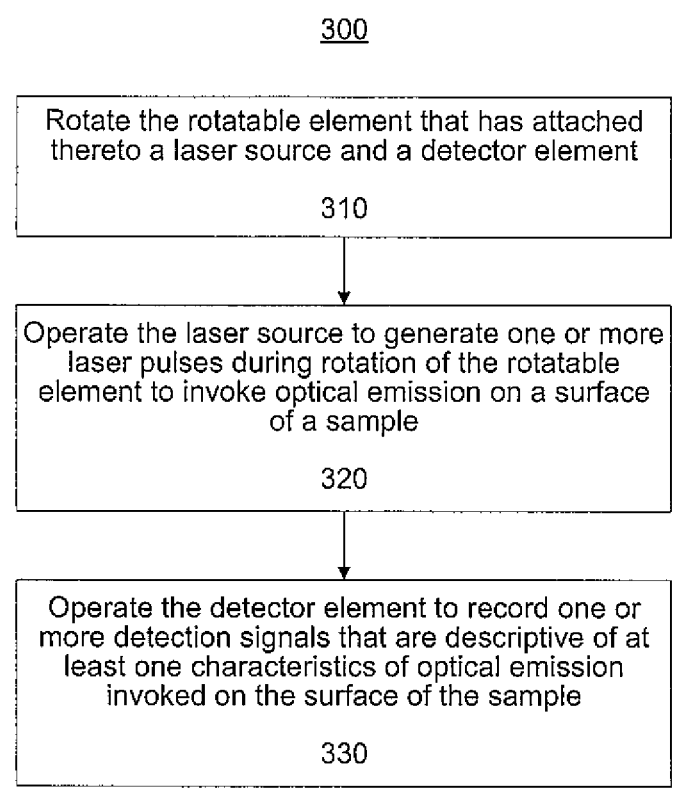
FIG. 7 depicts a flowchart illustrating a method according to an example embodiment.

FIG. 7 depicts a flowchart that illustrates steps of a method 300 for operating the detector assembly 210 described in the foregoing by a number of examples for analysis of elemental composition of the sample 229. The method 300 may be carried out under control of the control means 140. The method 300 comprises rotating the rotatable element 222 in accordance with desired rotation characteristics, as indicted in block 310. The desired rotation characteristics may define e.g. the direction(s) of rotation, the extent (e.g. angle) of rotation and the speed of rotation. The method 300 further comprises operating the laser source 221 to generate one or more laser pulses of desired characteristics during rotation of the rotatable element 222 to invoke optical emission from the surface of the sample 229, as indicated in block 320. In this regard, the desired characteristics may define e.g. the number of laser pulses, the duration of laser pulses, the repetition rate of laser pulses and energy of laser pulses. The method 300 further comprises operating the detector element 227 to record one or more detection signals that are descriptive of at least one characteristic of the optical emission invoked on the surface of the sample 229, as indicated in block 330. The detection signal(s) so obtained may be provided for analysis by the analysis means 130. The method 300 may be complemented or varied in a number ways, e.g. as described in the foregoing in various examples concerning operation and/or structure of the detector assembly 210.

Features described in the preceding description may be used in combinations other than the combinations explicitly described. Although functions have been described with reference to certain features, those functions may be performable by other features whether described or not. Although features have been described with reference to certain embodiments, those features may also be present in other embodiments whether described or not.

The invention claimed is:

1. A detector assembly for use in analysis of elemental composition of a sample by using optical emission spectroscopy, the detector assembly having a front end and comprising:
a rotatable element that is rotatable about an axis;
a laser source arranged in said rotatable element, the laser source provided for generating laser pulses for invoking optical emission on a surface of the sample, the laser source being arranged to generate laser pulses focused at a point at a first predefined distance greater than zero from said axis at a second predefined distance greater than zero from said front end of the detector assembly, such that rotating movement of the rotatable element moves said point along a circular trajectory having a radius that is equal to the first predefined distance on a plane that is at the second predefined distance from the front end of the detector assembly; and
an optical receiver arranged in said rotatable element, the optical receiver optically coupled to a detector by an optical fiber cable and the detector being for capturing optical emission invoked by said laser pulses.

2. The detector assembly according to claim 1, wherein said detector is provided outside the rotatable element.

3. The detector assembly according to claim 1, wherein said optical receiver comprises an end of said optical fiber cable.

4. The detector assembly according to claim 3, wherein said optical receiver further comprises one or more focusing optical elements for collecting light to the detector via the optical fiber cable.

5. The detector assembly according to claim 1, wherein the laser source is arranged at the first predefined distance from said axis and is further arranged to generate laser pulses in a direction parallel or substantially parallel to said axis.

6. The detector assembly according to claim 1, further comprising a beam focusing arrangement for focusing generated laser pulses at said first predefined distance from said axis at said second predefined distance from the front end of the detector assembly.

7. The detector assembly according to claim 1, wherein rotation of the rotatable element is limited to a predefined fraction of a full cycle of rotation.

8. The detector assembly according to claim 1, further comprising a housing substantially enclosing said rotatable element, wherein the housing comprises an opening, said laser pulses from said laser source exiting the detector assembly through said opening, and the optical emission from the surface of the sample entering the detector assembly through said opening.

9. The detector assembly according to claim 8, wherein the rotatable element is attached to the housing via a bearing to facilitate rotation of the rotatable element with respect to the housing.

10. The detector assembly according to claim 9, wherein the bearing comprises a rolling bearing having an inner race attached to the rotatable element and an outer race attached to the housing.

11. The detector assembly according to claim 1, wherein the rotatable element includes a radiation window, said laser pulses from said laser source exiting the detector assembly through said radiation window, and the optical emission entering the detector assembly through said radiation window.

12. The detector assembly according to claim 1, further comprising an actuator for inducing a rotating movement to said rotatable element.

13. The detector assembly according to claim 12, wherein said actuator is arranged for one of the following:
inducing rotation of a predefined extent in a predefined direction at a predefined speed in response to a trigger signal,
inducing rotation in response to a trigger signal, wherein the trigger signal carries information that specifies at least one of the following: an extent of rotation, a direction of rotation and a speed of rotation.

14. The detector assembly according to claim 1, wherein the laser source is arranged to generate one or more laser pulses during rotation of the rotatable element.

15. The detector assembly according to claim 1, wherein the laser source is arranged for one of the following:
generating a predefined number of laser pulses of predefined characteristics in response to a trigger signal,
generating laser pulses in response to a trigger signal, wherein the trigger signal carries information that specifies the number and characteristics of the laser pulses.

16. The detector assembly according to claim 1, arranged to provide laser-induced breakdown spectroscopy analysis.

17. An analyzer device for analysis of elemental composition of a sample, the device comprising,
a detector assembly according to claim 1, wherein the detector is arranged to record one or more detection signals that are descriptive of at least one characteristic of said optical emission for analysis of elemental composition of the sample by an analyzer, and
a controller for initiating an analysis cycle in response to a trigger signal, the controller arranged to cause the following during the analysis cycle:
rotate the rotatable element,
operate the laser source to generate one or more laser pulses during rotation of the rotatable element, and
operate the detector element to record one or more detection signals during rotation of the rotatable element.

* * * * *